(12) United States Patent
Shariati

(10) Patent No.: US 8,579,785 B2
(45) Date of Patent: Nov. 12, 2013

(54) SOURCE/SEED DELIVERY SURGICAL STAPLE DEVICE FOR DELIVERING LOCAL SOURCE/SEED DIRECLTY TO A STAPLE MARGIN

(76) Inventor: Nazly Makoui Shariati, Basking Ridge, NJ (US)

( * ) Notice: Subject to any disclaimer, the term of this patent is extended or adjusted under 35 U.S.C. 154(b) by 169 days.

(21) Appl. No.: 13/068,378

(22) Filed: May 10, 2011

(65) Prior Publication Data

US 2012/0289762 A1 Nov. 15, 2012

(51) Int. Cl.
*A61N 5/00* (2006.01)
*A61B 17/00* (2006.01)

(52) U.S. Cl.
USPC ............. 600/1; 606/143; 606/219; 227/176.1

(58) Field of Classification Search
USPC .......... 600/1–8; 606/139, 142, 143, 148, 215, 606/216, 219; 227/19, 175.1–182.1
See application file for complete search history.

(56) References Cited

U.S. PATENT DOCUMENTS

| 5,040,715 | A | * | 8/1991 | Green et al. ................. 227/176.1 |
|---|---|---|---|---|
| 5,906,573 | A | | 5/1999 | Aretz ................................ 600/3 |
| 6,254,601 | B1 | | 7/2001 | Burbank et al. ................. 606/45 |
| 6,293,899 | B1 | | 9/2001 | Sioshansi et al. ................. 600/3 |
| 6,471,630 | B1 | | 10/2002 | Sioshansi et al. ................. 600/1 |
| 6,514,193 | B2 | * | 2/2003 | Kaplan ............................ 600/7 |
| 6,575,887 | B1 | | 6/2003 | Schrayer ........................... 600/3 |
| 6,602,251 | B2 | | 8/2003 | Burbank et al. ................. 606/45 |
| 6,749,553 | B2 | | 6/2004 | Brauckman et al. ............. 600/3 |
| 6,764,488 | B1 | | 7/2004 | Burbank et al. ................. 606/51 |
| 7,604,586 | B2 | | 10/2009 | Wazer et al. ....................... 600/3 |
| 7,771,357 | B2 | | 8/2010 | Burbank et al. ............... 600/439 |
| 8,267,849 | B2 | * | 9/2012 | Wazer et al. ....................... 600/1 |
| 2002/0055666 | A1 | * | 5/2002 | Hunter et al. ..................... 600/1 |
| 2007/0244351 | A1 | | 10/2007 | Wazer ............................... 600/3 |
| 2008/0027343 | A1 | | 1/2008 | Fields et al. .................. 600/529 |
| 2008/0249503 | A1 | | 10/2008 | Fields et al. .................. 604/506 |
| 2009/0299125 | A1 | | 12/2009 | Wazer ............................... 600/7 |
| 2010/0015200 | A1 | | 1/2010 | McClain et al. .............. 424/423 |
| 2010/0239635 | A1 | | 9/2010 | McClain et al. .............. 424/423 |
| 2011/0006186 | A1 | | 1/2011 | Allen et al. ................... 248/694 |

FOREIGN PATENT DOCUMENTS

WO WO2011/011731 1/2011 ............... A61N 5/01

* cited by examiner

*Primary Examiner* — John Lacyk
(74) *Attorney, Agent, or Firm* — Ernest D. Buff; Ernest D. Buff & Assoc. LLC; Margaret A. LaCroix

(57) ABSTRACT

A source delivery surgical staple device delivers a source/seed to a staple margin. The surgical staple delivery device includes a main staple body segment hingedly attached to a second body segment. Each of the segments is appointed for engagement to dispense the sources/seeds and/or a surgical staple to the staple margin. The device also includes a cartridge removably attached and snapped onto the main staple body segment. The cartridge has at least one staple line appointed for housing surgical staples, and being operative to form at least one staple line of surgical staples, and at least one cut line. The cartridge also has at least one source/seed/brachy staple line forming a brachy or radioactive seeds and/or chemotherapy agent dosage source. The radioactive seeds have a radioactive and/or chemotherapy source supported by leg portions that are manipulated during insert for fastening the radioactive staples to tissue at an incision margin. With this arrangement, a hybrid of chemotherapy agent and radiation is delivered directly into the staple lines and different dosage brachy loads can be loaded in the cartridge.

10 Claims, 4 Drawing Sheets

[Prior Art]

[Prior Art]

SOURCE/SEED DELIVERY SURGICAL STAPLE DEVICE FOR DELIVERING LOCAL SOURCE/SEED DIRECLTY TO A STAPLE MARGIN

BACKGROUND OF THE INVENTION

1. Field of the Invention

The present invention relates to a source delivery surgical staple device for delivery of a source/seed directly to a surgical staple margin; and more particularly, to a source/seed delivery surgical staple device that provides for the direct delivery of sources or seeds containing radiation, and/or other tumor fighting means such as chemotherapy, in conjunction with surgical staples, whereby direct delivery of the seeds during surgery to the staple margin applies brachytherapy (local radiation source) to the staple margin in a controlled consistent manner.

2. Description of the Prior Art

Radiotherapy (radiation oncology, or XRT) is the medical use of ionizing radiation as part of cancer treatment to control malignant cells. Radiotherapy may be used for curative, adjuvant or palliative treatment. Total body irradiation (TBI) is a radiotherapy technique used to prepare the body to receive a bone marrow transplant. Radiotherapy has several applications in non-malignant conditions, such as the treatment of trigeminal neuralgia, severe thyroid eye disease, pterygium, pigmented villonodular synovitis, prevention of keloid scar growth, and prevention of heterotopic ossification. The use of radiotherapy in non-malignant conditions is limited partly by worries about the risk of radiation-induced cancers. Radiotherapy is commonly combined with surgery, chemotherapy, hormone therapy, Immunotherapy or mixtures thereof. Most common cancer types can be treated with radiotherapy in some way.

Brachytherapy, also known as internal radiotherapy, sealed source radiotherapy, curietherapy or endocurietherapy, is a form of radiotherapy where a radiation source is placed inside or next to an area requiring treatment. Brachytherapy is commonly used as an effective treatment for cervical, prostate, breast, skin and lung cancer and can also be used to treat tumors in many other body sites. Brachytherapy can be used alone or in combination with other therapies such as surgery, External Beam Radiotherapy (EBRT) and chemotherapy. Various methods of brachytherapy have been employed, including use of a vicryl patch/mesh construct having brachy therapy seeds sewn therein and applied over a staple line, or through utilizing radioactive surgical staples When a patient is deemed physiologically healthy, the operation of choice for lung cancer has been pneumonectomy, taking the entire lung out, or lobectomy, taking an anatomic unit along with its vascular supply and lymphatic drainage out. Instead of a pneumonectomy or lobectomy procedure, the physician may choose to perform a wedge resection. Wedge resectioning involves the removal of a triangle-shaped slice of tissue massing the tumor or some other type of tissue that requires removal, followed by surgical suturing via staple line or resection line. In general, repair of the wedge resection is simple by way of the staple/resection line and allows the underlying organ to retain its shape without distortion. Typically, the wedge resection leaves just a single stitch line. Despite the advantages concerning the operation procedure, wedge resections have not been considered an acceptable oncological resection method for cancer in patients who are fit physiologically to undergo lobectomies. What makes a wedge resection undesirable in cancer patients is the rate of recurrence of cancer at the staple line or resection line.

One method of brachy therapy involves implementation of a vicryl patch/mesh construct wherein brachy therapy seeds are sewn into the patch and applied on the line of the staples that the wedge resection was taken from. Generally mesh is provided with radioactive seeds through the intercostal access site. The width of the mesh is typically chosen based on at least 2-cm coverage of the lung parenchyma on each side of the staple line. $^{125}$I pellets incorporated within absorbable polyglycolate suture are typically woven into the customized mesh at 1-cm intervals. Landreneau et al., "*Intraoperative Brachytherapy Following Thoracoscopic Wedge Resection of State 1 Lung Cancer*", Chest Off. Pub. Of the Am. Coll. Of Chest Phys. Treatment is generally randomized to wedge resection alone versus wedge resection+brachy therapy using vicryl patch. It has been found that the wedge+brachy therapy yields a 1% local recurrence (LR), while wedge alone resulted in a 19% LR. However, despite the finding of positive results tending to the brachy therapy mesh+wedge resection treatment combinations, the procedure poses disadvantageous using the mesh. First, it's very operator dependent. Second, reproducibility is tedious, especially in video assisted cases.

Another method of brachy therapy proposes the uses of surgical staples having radioactive material sealed within a titanium tube to serve as legs of a tissue fastening system. Radioactive sources are appointed to be secured in position directly adjacent to the surgical resection. Dose distribution is precisely planned prior to the surgery to achieve the desired result. The delivery system is designed to be used in conjunction with the commercially available surgical stapling instruments widely used for VATS. The delivery system is constructed as a sidecar attachment that is adapted to attach onto a commercially available surgical stapler. The sidecar device contains the sources (with fastening legs)/radioactive staples in predetermined positions. After deployment of the surgical staples to excise the pulmonary wedge, the sidecar is independently activated to deploy the sources immediately adjacent to the surgical staples. "*Brachytherapy Delivery System for Treatment of Lung Cancer*", Source Production & Equipment Co., Inc., UMass, Mass. Med. Device Development Center, pp 1. Unfortunately, the armed staple and delivery system therein involving the sidecar on the commercial surgical staple results in a one-to-one relationship between the "sources"/radioactive staples and the number of surgical staples required for a given operation.

Disadvantages attending to heretofore disclosed methods and systems for delivery of brachy seeds include 1) difficulty in precise placement of the brachytherapy seeds/sources relative to the surgical margin, 2) separate surgical procedures for implantation of the brachytherapy weeks after surgery, and 3) exposure of radiation dose during implantation. Normally after a lobectomy patients have to wait between six to eight weeks to recover from surgery before the radiation treatment can begin. Most oncologists don't start treatment of any form until three months from the time of the lobectomy surgery. As a result, the patient is not immediately treated with the radiation and therefore risk of recurrence of the tumor increases.

There remains a need in the art for a source delivery stapler device that allows for precise delivery of radiation therapy to the surgical margin, while also providing a single step operation that allows the implantation of the radiation during a surgical re-sectioning procedure.

SUMMARY OF THE INVENTION

The present invention provides a source delivery stapler that delivers source staples (radiation; chemotherapy) and regular surgical staples to the surgical margin in a single step operation that allows for the implantation of the radiation during the surgical re-sectioning procedure. Particularly, the therapeutic staple delivery device allows for precise delivery of radiation therapy/sources to the surgical margin, thereby providing the ability to reduce surgical procedures and the ability for immediate radiation therapy to begin.

In a first embodiment, the source delivery surgical staple device that delivers a source/seed to a staple margin includes a main staple body segment hingedly attached to a second body segment, the segments being appointed to engage to dispense the sources/seeds and/or a surgical staple to the staple margin. The device also includes a cartridge removably attached and snapped onto the main staple body segment. The cartridge has at least one staple line appointed for housing surgical staples for forming at least one staple line of surgical staples, and at least one cut line. The cartridge also has at least one source/seed/brachy staple line forming a brachy or radioactive seeds and/or chemotherapy agent dosage source, the radioactive seeds having a radioactive and/or chemotherapy source supported by leg portions that are manipulated during insert for fastening the radioactive staples to tissue at an incision margin. Advantageously, a hybrid of chemotherapy agent and radiation is delivered directly into the staple lines and different dosage brachy loads can be loaded in the cartridge.

Also provided is a method of using the subject source delivery surgical staple device, comprising the steps of: (a) biopsy of the nodule; (b) performing wedge resection of the nodule; (c) preparing the source delivery surgical staple device of the subject invention; (d) loading the cartridge into the staple device; and (e) delivering the seeds to a surgical margin.

BRIEF DESCRIPTION OF THE DRAWING

The invention will be more fully understood and further advantages will become apparent when reference is had to the following detailed description of the preferred embodiments of the invention and the accompanying drawings, in which:

FIG. 1b.1 illustrates a prior art delivery system via the commercially available surgical stapling instrument (such as that widely used for video-assisted thoracoscopic surgery (VATS)) with the sidecar attached for delivery of seeds;

FIG. 1b.2 illustrates the prior art delivery system via the commercially available surgical stapling instrument with the sidecar being attached for delivery of seeds;

FIG. 1b.3 illustrates the staple lines with surgical staple lines and a seed line, showing a one-to-one application;

DETAILED DESCRIPTION OF THE INVENTION

Figure 1A:
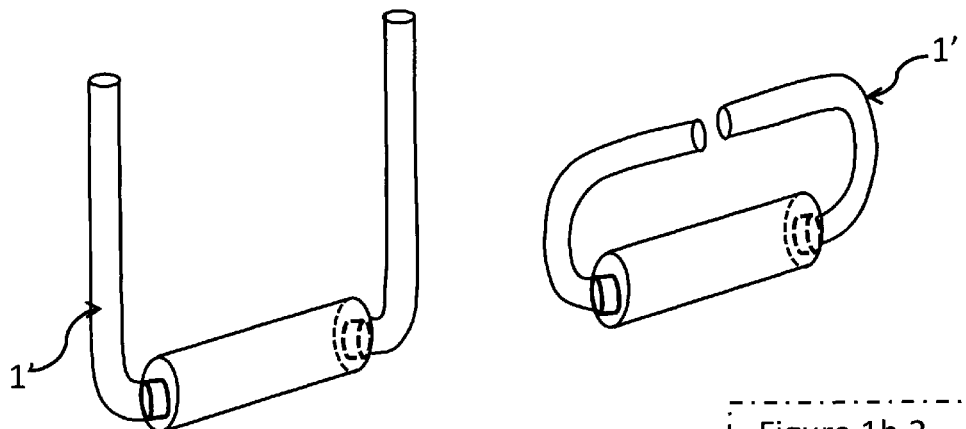
FIG. 1a illustrates a prior radioactive surgical staple/seeds.
Figure 1A:
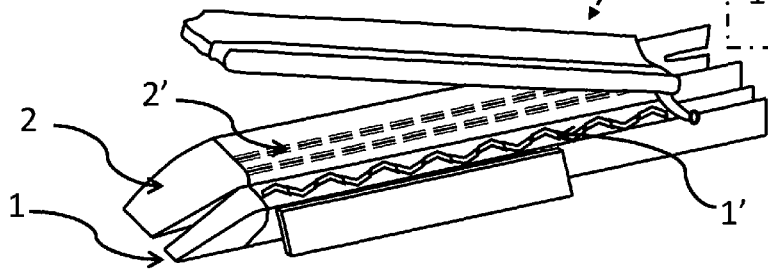
Figure 1A:
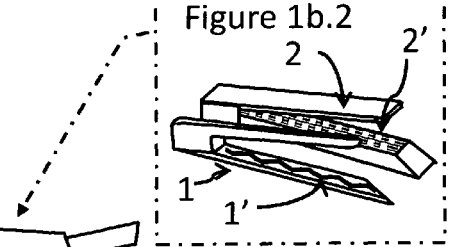
Figure 1A:
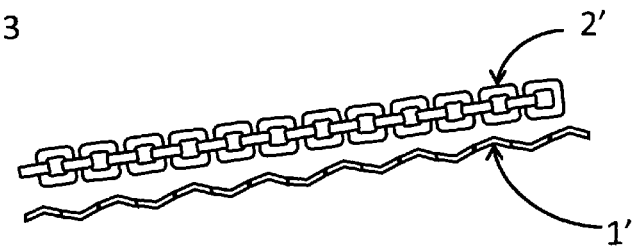
Figure 2:
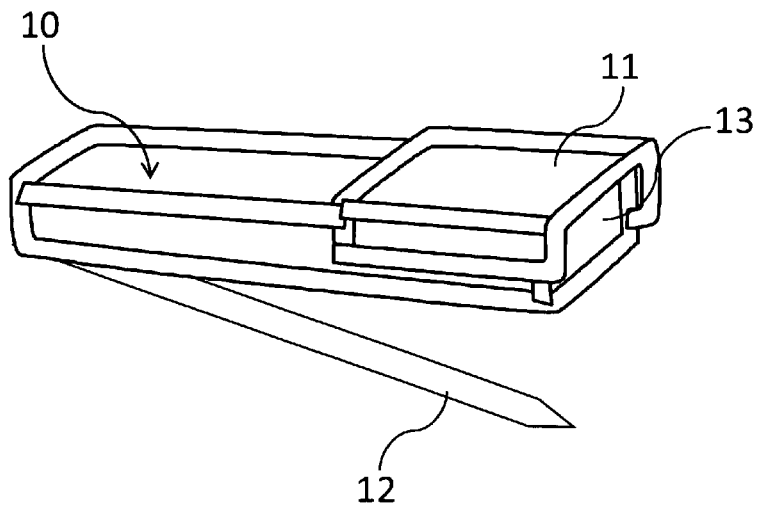
FIG. 2 illustrates a schematic view of the source delivery surgical staple device of the subject invention, showing the surgical stapler with a cartridge containing radioactive sources/seeds therein.
Figure 3:
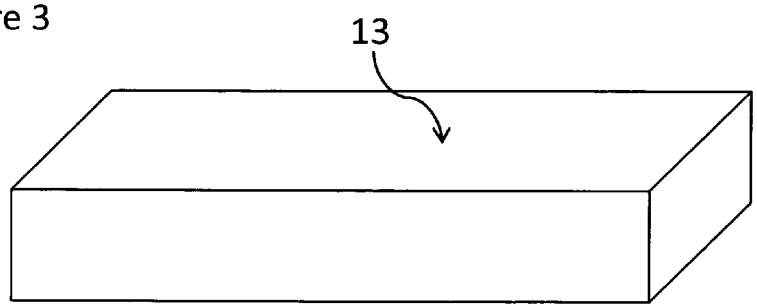
FIG. 3 shows a view of a cartridge for the source delivery surgical staple device of the subject invention.
Figure 4:
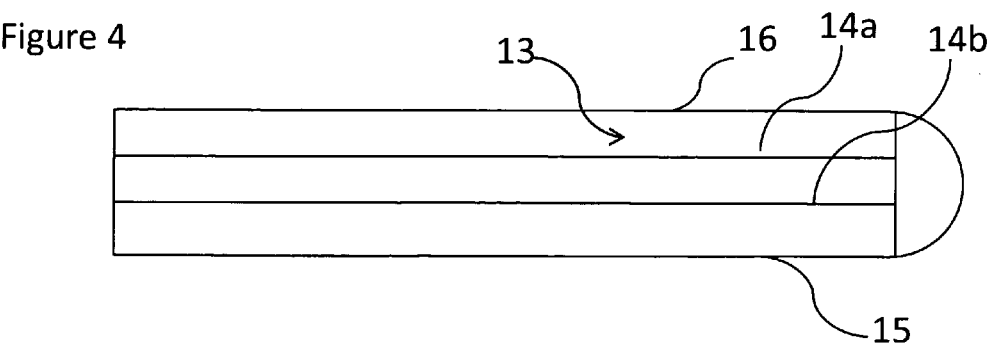
FIG. 4 shows a cross-sectional side view of the cartridge of FIG. 3.

This invention relates to a therapeutic stapler device and method of use thereof for delivery of sources, preferably radioactive staples and/or chemotherapy sources, to a surgical margin. The armed stapler/hybrid stapler/source delivery stapler of the subject invention provides a device that allows for precise delivery of radiation therapy to the surgical margin, while also providing a single step operation that allows the implantation of radiation during the surgical re-sectioning procedure. This not only provides for the ability to reduce surgical procedures, but also provides for immediate radiation therapy to begin.

The source delivery surgical staple device of the subject invention has been surprisingly and unexpectedly been found to allow for 1) precise placement of the brachytherapy seeds/sources relative to the surgical margin, 2) placement of the seeds during surgery, thus avoiding separate surgical procedures for implantation of the brachytherapy weeks after surgery, and 3) mitigation of exposure of radiation dose to the routineer during implantation. For example, with use of the current seed implantation methods discussed above, normally after a lobectomy, patients have to wait between six to eight weeks to recover from surgery before the radiation treatment can begin. As a result, most oncologists don't start treatment of any form until three months from the time of the lobectomy surgery. Thus, the patient is not immediately treated with the radiation and therefore risk of recurrence of the tumor increases. On the other hand, the source delivery surgical stapler of the subject invention allows immediate implantation of the seeds (radiation) during surgery via the surgical stapling phase, while also providing delivery of the seeds directly on the incision margin where local reoccurrence is most aggressive.

It has been surprisingly and unexpectedly found that the source delivery surgical staple device of the subject invention maximizes radiation exposure of tumor cells at the surgical margin. One of the major limitations of photon radiotherapy is that the cells of solid tumors become deficient in oxygen. Solid tumors can outgrow their blood supply, causing a low oxygen state known as hypoxia. Oxygen is a potent radiosensitizer, increasing the effectiveness of a given dose of radiation by preventing DNA damaging free radicals. Tumor cells in a hypoxic environment may be as much as 2-3 times more resistant to radiation damage than those in a normal oxygen environment. Given that data, the tumor cells left behind in the living tissue are really exposed to a higher level of oxygen as opposed to other organs. Hence the source delivery surgical staple device of the subject invention maximizes the radiation exposure of these tumor cells. Further, there is no need for extensive planning of radiation field to maximize delivery at the most compromised region/tissue. Theoretically, the tumor gets cut out and the tissue bed gets radiated most efficiently with minimal lung and heart toxicity.

FIG. 1a illustrates a prior radioactive surgical staple/seeds. FIG. 1b.1 illustrates a prior art delivery system via the commercially available surgical stapling instrument (such as that widely used for video-assisted thoracoscopic surgery (VATS)) with the sidecar attached for delivery of seeds. FIG. 1b.2 illustrates the prior art delivery system via the commercially available surgical stapling instrument with the sidecar being attached for delivery of seeds. FIG. 1b.3 illustrates the staple lines with surgical staple lines and a seed line, showing a one-to-one application. The delivery system for the seeds of FIG. 1a is shown at 1 in FIGS. 1b.1 and 1b.2. The delivery system 1 is a form of staple device that delivers seeds (FIG. 1a) and is designed to be used in conjunction with a commercially available surgical stapling instrument such as that shown at 2 in FIGS. 1b.1 and 1b.2, such as that widely used for VATS (Video-Assisted Thoracic Surgery). The seed delivery system device 1 is shown as a sidecar attached to the commercially available surgical stapler 2. The sidecar device 1 contains the sources (with fastening legs)/radioactive staples 1' as shown in FIG. 1a in predetermined positions. The commercially available surgical stapling instrument 2 contains surgical staples 2'. After deployment of the surgical staples 2' to excise a pulmonary wedge, the sidecar 1 is independently activated to deploy the sources 1' immediately adjacent to the surgical staples 2' as illustrated in FIG. 1b.3. The radioactive sources/seeds 1' are secured in position directly adjacent to the surgical staples 2' and are immobile. The fixed relationship of the sidecar 1 to the surgical stapler's 2 cartridge assures the fixed position of the sources 1' relative to the surgical staples 2', and therefore the surgical resection margin as in FIG. 1b.3. Unfortunately, the commercial staple 2 and side car 1 attached thereto results in a one-to-one relationship between the "sources"/radioactive staples 1' added and the number of surgical staples 2' required for a given operation.

Unlike the prior sidecar device, the source delivery surgical staple device of the subject invention is directed to a stapler device that includes a cartridge carrying radioactive sources, such as brachy seeds, so that the sidecar type construct is avoided.

The subject source delivery surgical staple device is adapted to deliver sources/seeds via brachytherapy (local radiation source) to a staple margin, and is constructed having a main staple body segment hingedly attached to a second body segment. The segments engage when dispensing surgical staples. A cartridge is snapped onto the main staple body segment. The cartridge includes at least one staple line, via first staple line of surgical staples; preferably the cartridge includes a second staple line of surgical staples. The cartridge further includes a cut line and brachy staple line of brachy or radioactive seeds and/or brachy staples having a radioactive source supported by leg portions that are manipulated during insert for fastening the radioactive staple to tissue at the margin. Preferably, brachy therapy seeds are to be incorporated in the stapler in the form of the staple at its base. The brachy seeds can be all in the form of Iodine seeds (I125) or alternate with Palladium (Pd103). Palladium seeds decay three times the rate of Iodine (I125) offering a higher initial dose rate to the target having particular treatment applications with more aggressive tumors. In another embodiment, a second generation stapler is provided. The stapler is similar to the first generation, but instead of using plain titanium material for the stapler, it comprises an alloy of titanium/cisplatin, etc.

The principal is to use a hybrid of chemotherapy agent directly into the staple line. Different dosage brachy loads can be loaded in the cartridge. Method steps involved include: 1) super D Biopsy of the nodule; and 2) wedge resection of the nodule—combo load brachy/chemo seeds, as opposed to making one row of staple carboplatin/platin.

Specific surprising and unexpected advantages of the subject source delivery surgical staple device include the allowance of more parenchymal preserving operations and less sacrifice/resection of the normal lung parenchyma (similar to the trend seen in breast cancer). The subject source delivery surgical staple device also allows immediate therapeutic brachy-radiation at the time of lung resectioning and hence minimizes the delay between the surgical resection and radiation therapy (normally after a lobectomy patients have to wait between 6-8 weeks to recover from surgery and most oncologists don't start treatment of any form until 3 months from the time of the lobectomy surgery). Moreover, the source delivery surgical staple device provides direct delivery of the radiation therapy (brachy) to the lung tissues where the majority of recurrences occur and further holds specifically in lung tissue because of the partial pressure of oxygen. The source delivery surgical staple device surprisingly and unexpectedly also enables delivery of oncological care to 75% of all lung cancer patients who would have been otherwise "non-surgical candidates". It enables sound oncological resection for elderly, medically unfit and advance stage lung cancer patients. It holds promise to be the primary mode of surgical intervention in all stages of lung cancer (anatomy allowing). Furthermore, the source delivery surgical staple device surprisingly and unexpectedly enables concurrent chemo/RTx at all stages of treatment with the least amount of radiation pneumonitis and toxicity, as well as less cardiac toxicity and esophagitis.

In referring to FIGS. 2-7, generally, the source delivery surgical staple device 10 includes a main staple body segment 11 hingedly attached to a second body segment 12. The segments engage when dispensing surgical staples.

Figure 7:
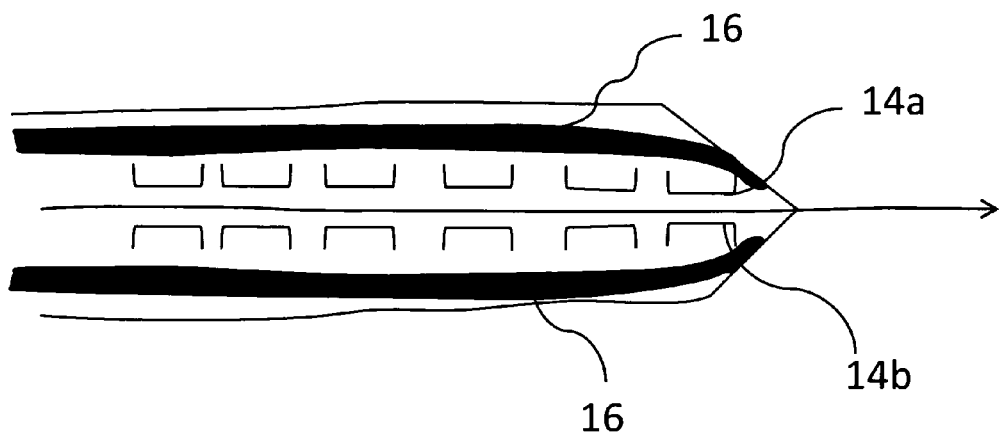
FIG. 7 shows the source delivery surgical staple device of the subject invention utilized in surgical stapling and radiotherapy treatment.

A cartridge 13 is snapped onto the main staple body segment 11. Cartridge 13 includes at least one staple line, shown as first staple line 14a of surgical staples; preferably cartridge 13 includes a second staple line 14b of surgical staples (FIG. 7). Cartridge 13 further includes a cut line 15 and brachy staple line 16 of brachy or radioactive seeds and/or brachy staples as shown in FIG. 5 at 34 having a radioactive source 35 supported by leg portion 36 that are manipulated during insert for fastening the radioactive staple 34 to tissue at the margin shown in FIG. 6 at 40.

Figure 5:
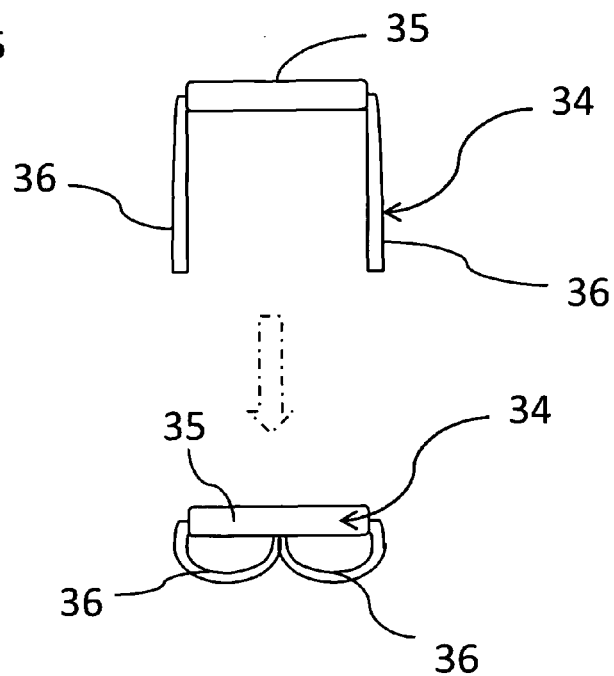
FIG. 5 illustrates an embodiment of the subject invention wherein the radioactive sources are provided as radioactive staples.
Figure 6:
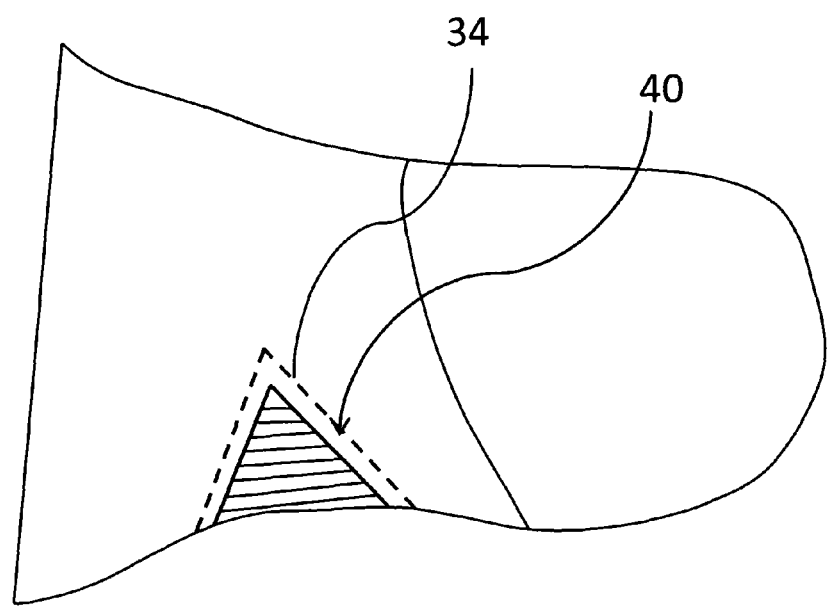
FIG. 6 shows a lung having a wedge resection.

Preferably, brachy therapy seeds are to be incorporated in the stapler in the form of the staple at its base (see 35 in FIG. 5). The brachy seeds can be all in the form of Iodine seeds ($^{125}$I). Preferably, the brachy seeds alternate with Palladium ($^{103}$Pd). Palladium seeds decay three times the rate of Iodine ($^{125}$I) offering a higher initial dose rate to the target having particular treatment applications with more aggressive tumors.

Second generation staples are also provided. The staplers are similar to the first generation, but instead of using plain titanium material for the staples, an alloy of titanium/with cisplatin etc. is used. The principal is to use a hybrid of chemotherapy agent directly into the staple line. Different dosage brachy loads can be loaded in the cartridge. Method steps involved include: 1) super D Biopsy of the nodule; and 2) wedge resection of the nodule—combo load brachy/chemo seeds making one row of staple carboplatin/platin.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A surgical staple device capable of contemporaneously delivering surgical staples and radioactive source staples to a surgical margin, comprising:
   a. a main staple body segment hingedly attached to a second body segment, said segments being appointed to engage for delivery of said surgical staples and said radioactive source staples to said surgical margin;
   b. a cartridge removably attached and snapped onto said main staple body segment;
   c. said cartridge having at least one surgical staple line comprising said surgical staples;
   d. said cartridge having at least one source staple line comprising said radioactive source staples, said radioactive source staples comprising brachytherapy seeds having at least one radioactive seed agent dosage source, said radioactive seed agent dosage source being supported by leg portions that are manipulated during insert for fastening said radioactive source staples to tissue at said surgical margin;

wherein said radioactive seed agent dosage source is capable of being delivered directly to said surgical margin and wherein different dosage brachytherapy seeds can be loaded in the cartridge.

2. A surgical staple device as recited by claim 1 comprising at least two surgical staple lines for delivery of at least two rows of surgical staples on said surgical margin.

3. A surgical staple device as recited by claim 1, wherein said source staple line further comprises chemotherapy agent dosage sources.

4. A surgical staple device as recited by claim 1, wherein said brachytherapy seeds comprise Iodine seeds (I125).

5. A surgical staple device as recited by claim 1, wherein said brachytherapy seeds comprise Palladium seeds (Pd 103).

6. A surgical staple device as recited by claim 1, wherein said brachytherapy seeds comprise Iodine seeds (I125) and Palladium seeds (Pd 103) having different decay rates offering different dosage levels for optimizing applications to tumors.

7. A surgical staple device as recited by claim 1, wherein said cartridge further comprises a carboplatin/platin staple line comprising carboplatin/platin staples.

8. A surgical staple device as recited by claim 1, wherein said surgical staple device is composed of titanium.

9. A surgical staple device as recited by claim 1, wherein said surgical staple device is composed of titanium alloy.

10. A method of using a surgical staple device that is capable of contemporaneously delivering surgical staples and radioactive source staples to a surgical margin, comprising the steps of:

a. biopsy of the nodule;

b. performing wedge resection of said nodule;

c. preparing said surgical staple device, said staple device comprising:

i) a main staple body segment hingedly attached to a second body segment, said segments being appointed to engage for delivery of said surgical staples and said radioactive source staples to said surgical margin;

ii) a cartridge removably attached and snapped onto said main staple body segment;

iii) said cartridge having at least one surgical staple line comprising said surgical staples;

iv) said cartridge having at least one source staple line comprising said radioactive source staples, said radioactive source staples comprising brachytherapy seeds having at least one radioactive seed agent dosage source, said radioactive seed agent dosage source being supported by leg portions that are manipulated during insert for fastening said radioactive source staples to tissue at said surgical margin;

wherein said radioactive seed agent dosage source is capable of being delivered directly to said surgical margin and wherein different dosage brachytherapy seeds can be loaded in the cartridge;

d. loading said cartridge into said staple device; and e. engaging said main body segment and said second body segment, thereby delivering said surgical staple to the tissue of a patient.

* * * * *